United States Patent [19]
Tammi et al.

[11] Patent Number: 5,622,180
[45] Date of Patent: Apr. 22, 1997

[54] DEVICE FOR MEASURING HEARTBEAT RATE

[75] Inventors: Tapio Tammi; Arto Pietilä, both of Oulu, Finland

[73] Assignee: Polar Electro Oy, Kempele, Finland

[21] Appl. No.: 986,684

[22] Filed: Dec. 8, 1992

[30] Foreign Application Priority Data

Dec. 9, 1991 [FI] Finland ................................ 915776

[51] Int. Cl.$^6$ ................................ A61B 5/0402
[52] U.S. Cl. ................................ 128/706; 128/690
[58] Field of Search ................................ 340/573, 502–505; 371/2.1, 4; 128/903, 690, 664, 666, 667, 668, 678, 689, 700, 695, 696, 706, 709

[56] References Cited

U.S. PATENT DOCUMENTS

| | | | |
|---|---|---|---|
| 3,082,414 | 3/1963 | Papaminas | 128/903 |
| 3,572,316 | 3/1971 | Vogelman et al. | 128/903 |
| 3,815,583 | 6/1974 | Scheidt | 128/903 |
| 4,038,976 | 8/1977 | Hardy et al. | 128/903 |
| 4,063,410 | 12/1977 | Welling | 128/903 |
| 4,129,124 | 12/1978 | Thalmann | 128/2.05 |
| 4,407,295 | 10/1983 | Sterner et al. | 128/670 |
| 4,409,983 | 10/1983 | Albert | 128/690 |
| 4,412,546 | 11/1983 | Barthels | 128/709 |
| 4,425,921 | 1/1984 | Fujiaski et al. | 128/690 |
| 4,489,731 | 12/1984 | Baumberg | 128/690 |
| 4,625,733 | 12/1986 | Saynajakangas | 128/687 |
| 4,630,613 | 12/1986 | Dennis | 128/903 |
| 4,814,751 | 3/1989 | Hawkins et al. | 128/903 |
| 4,952,928 | 8/1990 | Carroll et al. | 128/903 |
| 5,131,399 | 7/1992 | Sciarra | 128/903 |
| 5,243,992 | 9/1993 | Eckerle et al. | 128/690 |
| 5,355,664 | 10/1994 | Nagashima | 128/696 |

FOREIGN PATENT DOCUMENTS

| | | |
|---|---|---|
| 73126 | 9/1987 | Finland . |
| 2753165 | 11/1978 | Germany . |
| 2907570 | 8/1980 | Germany . |
| 2052752 | 1/1981 | United Kingdom ................ 128/666 |
| 2149514 | 6/1985 | United Kingdom ................ 128/696 |
| WO86/02538 | 5/1986 | WIPO . |
| 9116851 | 11/1991 | WIPO ................ 128/666 |

*Primary Examiner*—William E. Kamm
*Attorney, Agent, or Firm*—Finnegan, Henderson, Farabow, Garrett and Dunner, L.L.P.

[57] ABSTRACT

A device for measuring heartbeat rate that includes a device casing or wrist strap with skin contact electrodes, and a coil receiver for receiving telemetrically transmitted heartbeat signals for displaying heartbeat data either from the receiver, or the skin contact electrodes. The signals from the skin sensor are filtered, and subjected to an AGC device and pulse shaper. The received signals are amplified. A microcomputer, memory, and display are common to both the pulse shaped detected heartbeat signal and the amplified signal received from the transmitter.

8 Claims, 2 Drawing Sheets

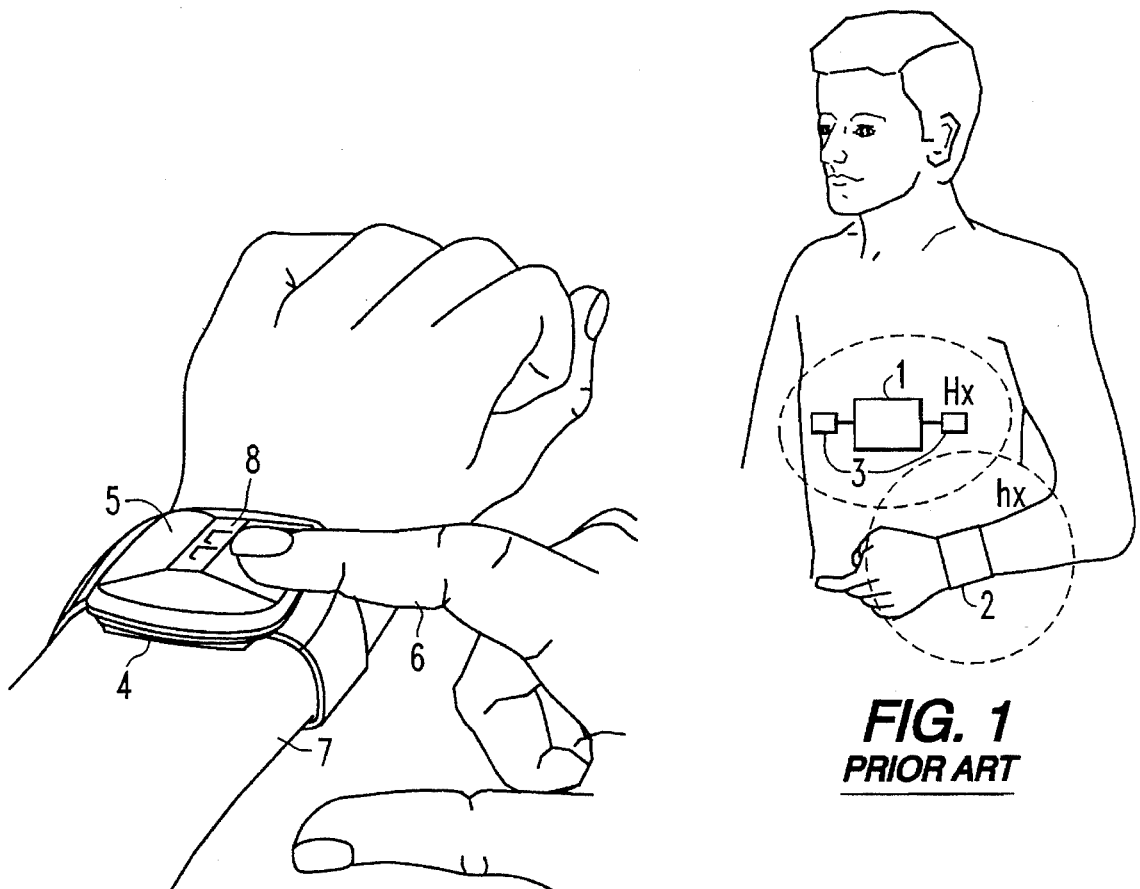
FIG. 2
PRIOR ART
FIG. 1
PRIOR ART
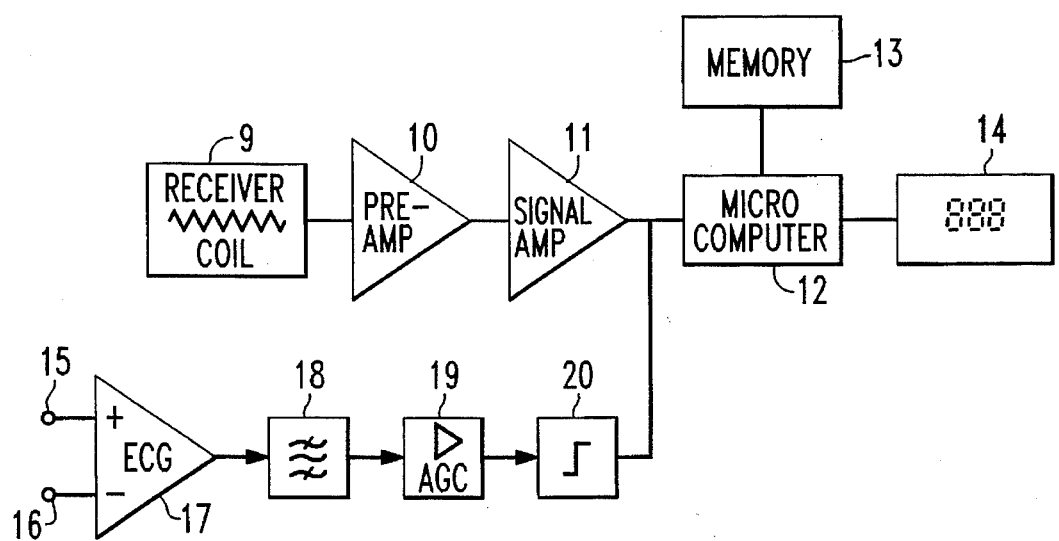
FIG. 3

DEVICE FOR MEASURING HEARTBEAT RATE

BACKGROUND OF THE INVENTION

This invention relates to a device for measuring heartbeat rate, and more particularly to a device for detecting and processing a signal carrying the heartbeat data and for indicating the heartbeat rate to the user of the device.

While participating in top sports, sports training and fitness training, it is important to measure the heartbeat rate reliably and without interruption during the performance, without the performance disturbing the measurement. Various handheld measuring devices based on the measurement of the ECG heartbeat rate signal from e.g. the user's fingertips have been designed for this purpose, as a well as a measuring devices based on telemetric wireless transmission between a separate transmitter attached to the body and a receiver worn on the wrist, cf. Finnish Patents 55761 and 68734.

Measurements based on contact are always somewhat inaccurate, depending on the user's anatomy and the way the device is held in the hand. Holding the device in the hand and observing the values on the display also needlessly draw the attention of the user to the device during the performance. On account of their reasonable price and measuring accuracy and ease of use, devices of this type have been used mainly for amateur performances. Wireless devices, in which the heartbeat rate signal is monitored continuously by means of ECG sensors that are stationary fixed to the body, have a measuring accuracy slightly better than that of the above-described hand-held devices, and due to the continuous measuring principle it has been possible to include pulse monitoring functions and statistical functions in these devices. The price of these devices has, however, been relatively high, which has limited their use mainly to professionals and sports clubs.

Continuous progress in electronic circuitry and manufacturing techniques has reduced the price of different measuring devices so that even casual users can now afford to buy them. However, the known devices are still divided into two groups according to their properties, which causes contradiction between the ease of use of the (handheld measuring devices), and the versatility of properties and measuring accuracy of the (wireless measuring devices).

SUMMARY OF THE INVENTION

The object of the present invention is to provide a device for measuring heartbeat rate, which avoids the above-mentioned disadvantage.

The objective and other advantages of the invention will be realized and attained by the device particularly pointed out in the written description and claims as well as the appended drawings.

To achieve these and other advantages and in accordance with the purpose of the invention, as embodied and broadly described the device includes first means for receiving and processing a telemetrically transmitted heartbeat rate signal, and second means for processing signals detected by electrodes or sensors integrated into either the device casing or wrist strap and corresponding to the detected heartbeat rate.

In the following the invention will be described by means of certain preferred embodiments with reference to the attached drawings, in which

BRIEF DESCRIPTION OF THE DRAWINGS

FIG. 1 illustrates a prior art telemetric way of heartbeat rate data transmission and measuring;

FIG. 2 illustrates a prior art way of measuring heartbeat rate based on skin contact;

FIG. 3 shows a device according to the invention in a block diagram form;

DESCRIPTION OF THE PREFERRED EMBODIMENTS

FIG. 1 shows a prior art telemetric heartbeat rate transmitter means 1 worn on the breast and a receiver means 2 worn on the wrist. ECG electrodes 3 in the transmitter means detect a person's ECG signal, and the signal is converted electronically into an AC signal supplying current to coils in the transmitter means 1. While passing through the coils, the AC signal generates a corresponding magnetic field around the coil within an area Hx. Correspondingly, a coil in the receiver means measures the magnetic field around the receiver means 2 within an area hx.

Figure 4:
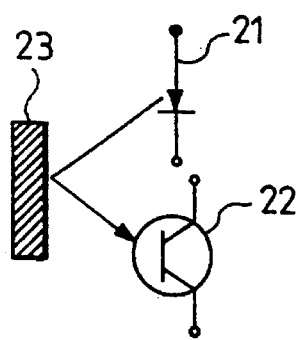
FIG. 4 shows an embodiment of sensors to be integrated into the casing of the device according to the invention.

FIG. 2 shows another prior art heartbeat rate measuring device worn on the wrist, where one ECG electrode 4 is formed by the bottom plate of the measuring device and the other ECG electrode 5 is formed by the casing of the measuring device. To measure the heartbeat rate, the casing 5 of the device (the other electrode) is pressed e.g. by the forefinger 6 of the other hand so that a corresponding force presses the bottom plate 4 against the wrist 7, and the electrodes 4 and 5 measure the heartbeat rate signal between the hands, which heartbeat rate signal may be processed by electronics enclosed within the casing 5 (cf. FIG. 4), and the result can be read from a display 8 provided in the casing.

FIG. 3 is a block diagram illustrating the device according to the invention. The device comprises two input lines, one for telemetric data transmission and the other for measurement based on skin contact; and common processing and display units. In the telemetric input line, the magnetic field detected by a receiver coil 9 is amplified in a sensitive preamplifier 10, whereafter the signal is applied to a signal amplifier 11. From the amplifier 11 the signal is applied to a microcomputer 12 for processing.

In one embodiment of the invention, in the line based on the skin contact principle, the electrodes detecting the heartbeat rate, disposed e.g. in the casing or wrist strap of the device of FIG. 2, are connected to differential input terminals 15 and 16 in an ECG preamplifier 17. The ECG heart signal from the preamplifier 17 is applied to a band filter 18 to remove distortion. Thereafter the signal is amplified by an AGC amplifier 19 to a level suitable for a pulse shaping means 20 and then the obtained signal is applied to the microcomputer 12. The heartbeat rate data calculated at the measuring stage can be stored by the microcomputer 12 in a semiconductor memory 13, from which the data can be read, processed further and displayed on a liquid crystal display 14. Various analyses can be performed on the measuring data by the microcomputer, such as analyses concerning the restoration of the pulse and the exceeding of safe pulse limits, and statistical analyses.

The different embodiments of the invention may also comprise other types of heartbeat rate measuring devices based on skin contact. Heartbeat rate can also be measured by means of light by measuring the intensity of the light passing through the tissue at the fingertip, for instance, as the intensity varies in pace with the heartbeat, which is mainly due to the fact that the amount of blood in the tissue varies with the heartbeat. In this case, the pulse detector may be e.g. a photodiode-phototransistor pair 21, 22 shown in FIG. 4, the phototransistor 22 replacing e.g. the ECG detector of FIG. 3. The lower surface of the nail, for instance, may serve as a reflecting plane 23.

A third way of measuring heartbeat rate is to utilize the principle known from blood pressure gauges, that is, to tonometrically monitor pressure impulses caused by the heartbeat in blood vessels (cf. e.g. Pressman & Newgard, "A Transducer for the Continuous External Measurement of Arterial Blood Pressure", IEEE Trans. Bio-Med. Electron., BME-10:73–81, 1963). In practice, the tonometric measurement is performed by exerting a force by means of a spring on a plate positioned on a vessel, and monitoring variation in the spring force as a function of time. To operate, the method requires that the vessel to be monitored is sufficiently close to the surface of the skin and that there is a bone below it, which forms a support surface and prevents the vessel from sinking in the tissue. One such vessel is e.g. the artery in the human wrist. A force sensor connected to the spring transmits the pressure variation in the monitored vessel to the device according to the invention in the form of pulses, from which the pulse frequency can be calculated directly. The force sensor may replace the ECG sensor 17 in the device shown in FIG. 3.

Figure 5:
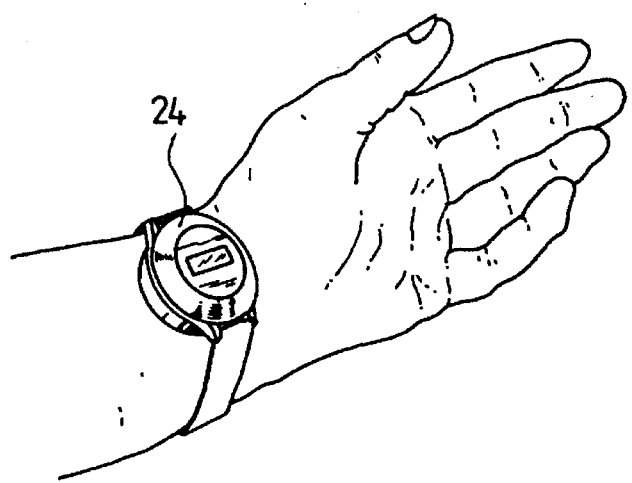
FIG. 5 shows a further embodiment of the device according to the invention.

As shown in FIG. 5, the device according to the invention, worn on the wrist at the artery, may thus measure the pulse frequency of the heart either in a wireless manner by means of the transmitter shown in FIG. 1 or directly from the artery. Depending on the situation and the conditions, the user may select either one of the measuring methods.

It is also possible to utilize other pulse frequency measuring methods based on skin contact within the scope of the invention; essential is that they are all based on bringing a suitable skin area into contact with the casing, wrist strap, or other similar part of the measuring device.

The device according to the invention thus comprises means for receiving a telemetrically transmitted heartbeat rate signal, the means comprising a receiver coil 9 and amplifiers 10 to 11; and means for processing heartbeat rate signals detected by electrodes or sensors integrated into the casing of the device, such as the casing and/or bottom 4 in FIGS. 2 and 5. The selection between the two methods can be made by the user according to the situation. The selection is preferably made simply by applying the selected method, the device thus immediately recognizing the presence of the heartbeat data and automatically picks them up for processing from the appropriate line.

It is obvious to one skilled in the art that the different embodiments of the invention are not restricted to the above-described example, but they may vary within the scope of the following claims.

What is claimed is:

1. A system for measuring a heartbeat rate of an individual, comprising a device having a casing for strapping to a wrist of the individual;

receiving means contained in the casing of the device for receiving heartbeat rate signals telemetrically transmitted from an area remote from the wrist of the individual to whose wrist the device is strapped;

first processing means contained in the casing of the device for processing the received telemetrically transmitted heartbeat rate signals;

sensor means mounted to the casing of the device for detecting heartbeat rate signal emanating from the individual to whose wrist the casing of the device is strapped when the sensor means engages the individual;

second signal processing means contained in the casing of the device for processing heartbeat rate signals sensed by the sensor means, the second signal processing means of the device including a series connected filter, gain control circuit, and a pulse shaper, coupled to a third signal processing means;

the third signal processing means, contained in the casing of the device for receiving and processing the processed heartbeat rate signals from either one of the receiving means and the sensor means; and display means contained in the casing of the device and having an input electrically connected to the third signal processing means for displaying either the third processed telemetrically received heartbeat rate signals or the sensed heartbeat rate signals.

2. The system of claim 1 wherein the sensor means includes electrodes on a surface of the casing for detecting heartbeats at times when said surface engages the wrist of the individual.

3. The system of claim 1 wherein the sensor means includes a tonometric sensor in a surface of the casing of the device for detecting pressure variation in a blood vessel close to a surface of skin of the individual at times when the sensor engages the skin surface of the individual.

4. The system of claim 1 wherein the sensor means includes photoelectric components for detecting variations in intensity of light passing through tissue of the individual at times when the sensor means opposingly engages the tissue.

5. The system of claims 2, 4, 3 or 1 wherein the third signal processing means of the device comprises a microcomputer and memory, the microcomputer being connected to store signals in the memory from the receiving means and the sensor means.

6. The system according to claim 4 or 1 wherein the sensor means of the device includes photoelectric components for detecting variations in intensity of light passing through finger tissue of the individual at times when the sensor means opposingly engages the finger tissue.

7. The system according to claim 2, 4, 3 or 1 wherein the receiving means comprises a magnetic coil mounted to the casing of the device.

8. The system of claim 1 further comprising a transmitter for transmitting by wireless telemetric transmission heartbeat rate signals from a location remote from the casing of the device and the wearer's wrist.

* * * * *